United States Patent
Song et al.

(10) Patent No.: US 10,031,255 B2
(45) Date of Patent: Jul. 24, 2018

(54) MULTI-DIMENSIONAL NUCLEAR MAGNETIC RESONANCE METHODS FOR CHARACTERIZING FLUIDS

(71) Applicant: SCHLUMBERGER TECHNOLOGY CORPORATION, Sugar Land, TX (US)

(72) Inventors: Yi-Qiao Song, Newton Center, MA (US); Bernhard Bluemich, Roetgen (DE)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 971 days.

(21) Appl. No.: 14/223,615

(22) Filed: Mar. 24, 2014

(65) Prior Publication Data

US 2015/0268323 A1    Sep. 24, 2015

(51) Int. Cl.
  *G01V 3/00*   (2006.01)
  *G01V 3/32*   (2006.01)
  *G01N 24/08*  (2006.01)
  *G01R 33/46*  (2006.01)
  *G01R 33/44*  (2006.01)

(52) U.S. Cl.
  CPC ............. *G01V 3/32* (2013.01); *G01N 24/081* (2013.01); *G01R 33/4633* (2013.01); *G01R 33/448* (2013.01)

(58) Field of Classification Search
  CPC .... G01V 3/32; G01N 24/081; G01R 33/4633; G01R 33/448
  USPC .......................................................... 324/303
  See application file for complete search history.

(56) References Cited

U.S. PATENT DOCUMENTS

| | | | |
|---|---|---|---|
| 5,280,244 A * | 1/1994 | Hinks | G01R 33/56509 324/306 |
| 6,462,542 B1 | 10/2002 | Venkataramanan et al. | |
| 6,856,132 B2 * | 2/2005 | Appel | G01V 3/32 324/303 |
| 7,622,919 B2 * | 11/2009 | Song | G01N 24/081 324/307 |
| 8,471,559 B2 | 6/2013 | Taherian et al. | |
| 2002/0021127 A1 * | 2/2002 | Hennig | G01R 33/5613 324/307 |
| 2003/0234648 A1 * | 12/2003 | Ganesan | G01V 3/32 324/303 |
| 2004/0119471 A1 | 6/2004 | Blanz et al. | |
| 2004/0253743 A1 | 12/2004 | Freed | |

(Continued)

FOREIGN PATENT DOCUMENTS

| | | | | |
|---|---|---|---|---|
| EP | 2177924 A1 * | 4/2010 | | G01N 24/08 |
| JP | 2010071839 A * | 4/2010 | | G01N 24/08 |

OTHER PUBLICATIONS

Dickinson, et al., "Structural comparison of petroleum fractions using proton and 13C n.m.r. spectroscopy", Fuel, vol. 59, Issue 5, May 1980, pp. 290-294.

(Continued)

*Primary Examiner* — Susan Lee

(57) ABSTRACT

Methods are disclosed for characterizing samples containing a plurality of molecular species through the use of multi-dimensional spectra obtained by processing of measurements resulting from pulse sequences combining NMR spectroscopy and NMR relaxation techniques.

42 Claims, 7 Drawing Sheets

(56) References Cited

U.S. PATENT DOCUMENTS

| | | | |
|---|---|---|---|
| 2005/0134275 A1* | 6/2005 | Frydman | G01N 24/08 324/321 |
| 2007/0238969 A1* | 10/2007 | Song | A61B 5/055 600/410 |
| 2008/0150525 A1* | 6/2008 | Song | G01N 24/08 324/307 |
| 2010/0072995 A1 | 3/2010 | Nishiyama | |
| 2010/0134104 A1 | 6/2010 | Song et al. | |
| 2011/0234220 A1 | 9/2011 | Mitchell et al. | |
| 2012/0049844 A1* | 3/2012 | Leveridge | G01V 3/32 324/303 |
| 2012/0062229 A1 | 3/2012 | Topgaard | |
| 2012/0169334 A1 | 7/2012 | Hopper et al. | |
| 2013/0002246 A1* | 1/2013 | Venkataramanan | G01V 3/14 324/303 |
| 2013/0176026 A1* | 7/2013 | Song | G01N 24/081 324/309 |
| 2014/0232391 A1* | 8/2014 | Kadayam Viswanathan | G01V 3/32 324/303 |

OTHER PUBLICATIONS

Hasan, et al., "Structural Characterization of Paero Crude Oil by FT-Infrared and 1H N.M.R. Spectroscopy", Fuel Science and Technology International, vol. 10, Issue 9, 1992, pp. 1407-1420.

Hasan, et al., "Structual characterization of Saudi Arabian extra light and light crudes by 1H and 13C n.m.r. spectroscopy", Fuel, vol. 68, Issue 6, Jun. 1989, pp. 801-803.

Hasan, et al., "Structural characterization of Saudi Arabian heavy crude oil by n.m.r. spectroscopy", Fuel, vol. 62, Issue 5, May 1983, pp. 518-523.

Hasan, et al., "Structural characterization of Saudi Arabian medium crude oil by n.m.r. spectroscopy", Fuel, vol. 64, Issue 6, Jun. 1985, pp. 839-841.

Scotti, "Molecular Structure and Intermolecular Interaction of Asphaltenes by FT-IR, NMR, EPR", Structures and Dynamics of Asphaltenes, Plenum Press, New York, 1998, pp. 79-113.

International Search Report and Written Opinion issued in related PCT application PCT/US2015/022258 dated Jun. 26, 2015, 13 pages.

* cited by examiner

MULTI-DIMENSIONAL NUCLEAR MAGNETIC RESONANCE METHODS FOR CHARACTERIZING FLUIDS

FIELD

The subject disclosure generally relates to testing of fluids obtained from geological formations and, more particularly, the subject disclosure relates to testing of fluids obtained from geological formations using nuclear magnetic resonance (NMR).

BACKGROUND

Crude oil, also called petroleum, is constituted from a complex mixture of many different molecules of different size and shape. The molecules may come from different molecular groups, such as alkanes, aromatics, waxes, and asphaltenes. The chemical composition of a crude oil plays an important role in determining the value of the crude, as well as the strategy for efficient production.

Crude oils are classified primarily according to their geographic origin, their API (American Petroleum Institute) gravity, and their sulfur content. The geographic origin is of interest due to transportation costs. Well-known locations are West Texas Intermediate, Brent (North Sea), and Oman. The API gravity is a measure of the oil quality. The API gravity has been defined to scale with the price of the oil. As lighter oils yield more gasoline, they are considered to be higher quality and therefore more expensive. Lighter oils have higher values of API gravity.

Crude oil is typically processed by distillation at atmospheric pressure. This is why crude oils are also characterized by their distillation yields. Distillation discriminates compounds based on the boiling points and not their chemical structure. It is thus a discrimination method based on molecular physics. With increasing temperature, the standard fractions are C1 to C4 compounds, naphtha, kerosene, gas oil, and atmospheric residue, which cannot be further distilled without the risk of cracking.

The chemical composition of oils and their fractions are generally analyzed by chromatographic and spectroscopic methods. Gas chromatography (GC) is frequently used for fractionation of viscous oils, and in many cases also high-performance liquid chromatography (HPLC) and supercritical fluid chromatography (SFC). The most common spectroscopic method of analysis is infrared spectroscopy (IR) as it can identify different chemical groups. Similar detail is provided by high-resolution NMR spectroscopy (ASTM Test Method D5292: Aromatic Carbon Contents of Hydrocarbon Oils by High-Resolution Nuclear Magnetic Resonance Spectroscopy) without the need of a reference standard and to a lesser degree by low-resolution NMR (ASTM Test Method D4808: Hydrogen Content of Light Distillates, Middle Distillates, Gas Oils and Residua by Low Resolution Nuclear Magnetic Resonance Spectroscopy). Another approved test method for compositional analysis of hydrocarbons is mass spectrometry (MS).

Saturates are non-polar normal alkenes, or n-paraffins, branched alkanes or iso-paraffins, and cyclo-alkanes or naphtenes. They are the largest single source of hydrocarbon or petroleum waxes with paraffin wax as the major constituent. Aromatics contain one or more ring structures similar to benzene with connections by aromatic double bonds. They are chemically and physically very different from paraffins and naphtenes. Resins are heavy liquids or sticky amorphous solids which are soluble in the petroleum fluid. Resins are understood to be molecular precursors of asphaltenes. Resins have polar head groups that surround asphaltenes and aliphatic tails that extend into the oil. As such, they stabilize asphaltene dispersions in oil. They can be converted to asphaltenes upon oxidation. Asphaltenes are defined as the petroleum fraction that is insoluble in light alkanes but soluble in toluene or dichloromethane. Their molecular structure is ill-defined but contains aromatic polycyclic clusters variably substituted with alkyl groups as well as hetero-atoms like N, S, O, and trace metals like Ni, V, Fe. Asphaltenes are dispersed as colloids in the oil and crack before boiling.

In addition to their carbon and hydrogen components, many oils contain trace amounts of other elements such as rare earth elements (e.g., Sc, Y, La, Ce, Pr, Nd, Pm, Sm, Eu, GD, Tb, Dy, Ho, Er, Tm, Yb, Lu), which include the lanthanides. Complexes with lanthanides find use in NMR spectroscopy as chemical shift reagents which spread the frequency range of the NMR signals from different chemical groups over a larger range.

High-resolution NMR spectra of crude oils have been reported by Hasan et al. See, e.g., Hasan, M. U., et al., "Structural characterization of Saudi Arabian heavy crude oil by NMR spectroscopy," *Fuel* 62, pp. 518-523 ((1983); Hasan, M. U., et al., "Structural characterization of Saudi Arabian medium crude oil by NMR spectroscopy," *Fuel* 64, pp. 839-842 (1985); Hasan, et al., "Structural characterization of Saudi Arabian extra light and light crudes by $^1$H and $^{13}$C NMR spectroscopy," *Fuel* 68, p. 801 (1989); and Hasan, M. U., et al., "Structural characterization of Panero crude oil by FT-infrared and $^1$H NMR spectroscopy," *Fuel Sci. Tech. Int.* 10, pp. 1407-1420 (1992). Hasan et al. divide the proton chemical shift range into four windows, namely, a window for aromatic protons $H_{arom}$ (6.0-9 ppm), and three windows for aliphatic protons $H_{sat}$ (0.0-4.0 ppm), namely $H_\alpha$ (2.0-4.0 ppm), $H_\beta$ (1.0-2.0 ppm), and $H_\gamma$ (0.5-1.0 ppm). A slightly different definition of windows has been reported for asphaltenes: aromatic protons $H_{arom}$ (6.5-9 ppm), $H_\alpha$ (2.0-4.0 ppm), $H_\beta$ (1.0-2.0 ppm), and $H_\gamma$ (−1.0-1.0 ppm). See, e.g., Scotti, R. and Montanari, L., "Molecular structures and intermolecular interaction of asphaltenes by FT-IR, NMR, EPR," *Structures and Dynamics of Asphaltenes* (O. C. Mullins and E. Y. Sheu), Plenum Press, New York (1998). The fractions of protons in these ranges vary in an interlinked fashion with the composition of the oil. The spectroscopic signals may be quantified in terms of relative intensities. For the protons in asphaltenes, Dickinson defines $1/n = I_{H\alpha}/(I_{H\alpha} + I_{H\beta} + I_{H\gamma})$. See, Dickinson, E. M., "Structural comparison of petroleum fraction using proton and $^{13}$C NMR spectroscopy," *Fuel* 59 pp. 290-294 (1988).

When measured at a constant applied field, the positions of lines in a high-field high-resolution $^1$H NMR spectrum may vary by up to 0.3 ppm and more due to susceptibility effects from the oils and from different filling heights in the sample tubes. When measured with respect to internal TMS (the tetramethylsilane standard for measuring chemical shift), there seem to be no obvious shift variations within better than 0.01 ppm accuracy. The achievable chemical-shift resolution increases with decreasing viscosity such that low-viscosity oils give spectra with the highest resolutions. At elevated temperature, the spectral resolution improves. When changing the temperature from room temperature to 50° C., the change in resolution is rather small while at 80° C. it greatly improves. The four different chemical shift regions can clearly be identified and the chemical shifts of the most prominent peaks and the amplitude ratios of the largest peaks of six oil samples are summarized in Table 1 below.

TABLE 1

Chemical shifts δ relative to internal TMS of the largest peaks

| Oil | $\delta_{H\gamma}$ [ppm] | $\delta_{H\beta}$ [ppm] | $\delta_{arom1}$ [ppm] | $\delta_{arom2}$ [ppm] | $A_{H\beta}/A_{H\gamma}$ | $A_{Harom}/A_{H\gamma}$ | $I_{Harom}/I_{total}$ [%] |
|---|---|---|---|---|---|---|---|
| 11 | 0.87 | 1.24 | 6.97 | 7.39 | 1.8 | 0.018 | 5.0 |
| 13 | 0.87 | 1.25 | 6.82 | 6.98 | 1.4 | 0.025 | 4.7 |
| 20 | 0.87 | 1.27 | 6.84 | 7.01 | 0.7 | 0.033 | 3.8 |
| 21 | 0.87 | 1.27 | 6.85 | 7.01 | 2.4 | 0.018 | 2.2 |
| 24 | 0.87 | 1.28 | 6.85 | 7.03 | 2.7 | 0.005 | 0.7 |
| 25 | 0.88 | 1.24 | 6.81 | 6.93 | 2.3 | 0.028 | 4.2 |

The most prominent signals in dead oil are from the β and γ protons. They are separated by 0.4 ppm and promise to be detectable by downhole NMR spectroscopy with an instrument providing medium resolution as low as 0.2 ppm. Each of these lines is composed from contributions of thousands of molecules but the dominant contributions are from aliphatic $CH_2$ for the β resonances and from $CH_3$ for the γ resonance. Differing compositions of oils give rise to variations of the peak positions and line-shapes. The chemical shift of the strong peak of the γ protons shows the least variation among all the oils. This identifies this peak as an internal chemical shift reference for down-hole NMR spectroscopy. The higher the chemical shift, the larger the variation of the strongest peaks from oil to oil. However, an assignment to chemical groups of individual molecules is not possible due to the large number of molecules present in crude oils (up to 50,000).

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In embodiments, methods are described for characterizing hydrocarbon samples containing a plurality of molecular species through the use of multi-dimensional spectra obtained by processing of measurements resulting from pulse sequences combining NMR spectroscopy and NMR relaxation techniques. In one embodiment NMR relaxation techniques are combined with NMR spectroscopy techniques in a first combined pulse sequence π/2-τ1-n/2-Δ-CPMG, where π/2 is a ninety degree (90°) precession alignment pulse, τ1 is a spectroscopy time period that is incremented multiple times during an experiment, Δ is a small fixed period of time, and CPMG (which utilizes a second time period τ2) is the standard known Carr-Purcell-Meiboom-Gill pulse sequence used in measuring spin-spin relaxation times (T2). CPMG uses the following pulse sequence: $[\pi/2\text{-te}/2\text{-}(\pi\text{-te})_N]$, where the sequence segment (π-te) is repeated N times. Signal acquisition is performed during each "te" period between two adjacent π pulses. The time period te is referred to as an echo time. The decay time T2 of the i-th echo is determined by τ2=i*te. Typically, signal is acquired for all N echoes from one execution of the pulse sequence in order to obtain the signal decay curve as a function τ2. Thus, the combined sequence has a first portion (before the Δ) that is the spectroscopy portion of the sequence, and a second portion (CPMG) that is the relaxation portion of the sequence. If desired, the combined pulse sequence can be modified (shortened) so that the spectroscopy portion is π/2-τ1, and the CPMG sequence utilizes the π/2-τ1 portion as the beginning of its sequence [π/2-τ1, te/2, $(\pi\text{-ACQ})_N$], where n is the number of 180 degree pulses, and τ2=N*te.

Using the first combined pulse sequence (or its modification), signal measurements are made that can be described according to $$M(\tau 1, \tau 2) = \int f(\chi, T2)\cos(\chi * \tau 1 * \omega)e^{(-\frac{\tau 2}{T2})}d\chi dT2, \quad (1)$$

where ƒ is a distribution function proportional to the density of spins with the specific chemical shift χ and spin-spin relaxation time T2. The period Δ is often kept small so that a minimum amount of relaxation occurs. Even though T2 relaxation is effective during the τ1 period, it appears as line-broadening in the f(χ,T2) function. Other effects may also contribute to the line-broadening such as magnetic field inhomogeneity. Thus Eq. (1) can be used to analyze the data. Data analysis is performed by conducting a Fourier transform along the τ1 direction and then a Laplace inversion along the τ2 direction thereby generating a two-dimensional spectrum with peaks identifying different molecules present in the sample. The two-dimensional spectrum is optionally plotted on a graph utilizing chemical shift (ppm) as one axis and relaxation time T2 as the other axis, thereby separating signals from molecules with the same chemical shift but different T2 times and signals from molecules with the same T2 times but different chemical shifts. An integration of the signal under a region around a peak provides the total signal attributed to the respective peak, and thus its weight.

In another embodiment, the order of the portions of the sequence is reversed such that a CPMG sequence is followed by a spectroscopy acquisition (e.g., CPMG-ACQ). Data analysis is performed in the same manner with a Fourier transform along the τ1 direction and then a Laplace inversion along the τ2 direction thereby generating a two-dimensional spectrum with peaks identifying different molecules present in the sample.

In another embodiment, NMR diffusion measurement techniques are combined with NMR spectroscopy techniques and relaxation techniques to provide a three-dimensional spectrum (χ, D and T2).

In one aspect, data analysis may be performed in different manners. In one embodiment, a Fourier transform along a first direction is performed followed by a Laplace inversion along another. In another embodiment, a Laplace transform is performed in the second direction followed by a Fourier transform in the first direction. In another embodiment, the distribution function is parameterized in terms of a plurality of parameters, such as one peak for water, one for each of $CH_2$, $CH_3$, $CH_4$ (methane), ethane, etc. Each peak is characterized by a chemical shift, and one or more of a relaxation or diffusion, and an amplitude. Then, using a forward model, an expected signal is calculated for a particular combination of molecules (sample). The measured data is then compared with the expected signal, and the parameters (e.g., one or more of the amplitudes, the relaxation times and peak widths) are adjusted until the expected signal generated from the model is consistent with the measured data, or until a best fit is found. The results may be displayed in any of many ways.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein:

FIGS. 5b and 5c are geography maps of respectively the aliphatic and aromatic regions of FIG. 5a.

FIGS. 6a and 6b are projections along chemical shift and T2 dimensions for selected regions of FIG. 5a.

FIGS. 7a and 7b are projections along frequency and T2 dimensions for non-selected regions of the two-dimensional spectrum of FIG. 5a.

DETAILED DESCRIPTION

Figure 1A:
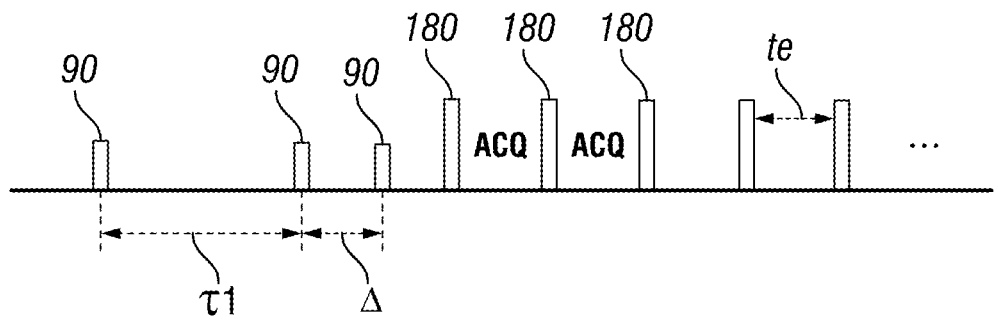
FIG. 1a is a schematic of a first T2 plus spectroscopy combined pulse sequence.

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice.

A simple NMR spectroscopy experiment can be performed by applying a single radio frequency (RF) pulse that rotates the spin magnetization of the atoms of the molecules of a sample by 90 degrees or any other non-zero rotations. The precession of the spins of the molecules resulting from the pulse can be recorded as a time-domain signal, and a Fourier transform of the time-domain signal provides a frequency spectrum of the molecules of the sample. The frequency of the precession is written as $$f = (1+\chi S)\gamma B_0 \quad (3)$$

where $B_0$ is the applied magnetic field, $\gamma$ is the gyromagnetic ratio, and $\chi$ is the frequency shift factor that is molecule-specific. In practice, this frequency shift is often described as the difference ($\chi$) between the test molecule and a reference molecule usually selected to be tetra-methyl-silane (CH3) 4-Si (TMS). The precession frequency of the reference molecule is often denoted $f_0$ with the corresponding angular velocity $\omega_0 = 2\pi f_0$. Tables for the $\chi$ values for many different molecules are available in the art.

The RF "pulse sequence" for NMR spectroscopy that utilizes a single pulse is usually written as $\pi/2$-ACQ, where $\pi/2$ represents a ninety degree pulse and ACQ denotes signal acquisition, which is the use of the NMR system to receive and detect signal from the precessing spins. The signal received and detected in this fashion in often called free-induction decay (FID). A similar pulse sequence for NMR spectroscopy is the sequence $\pi/2$-te/2-$\pi$-te/2-ACQ where to is a time delay usually on the order of microseconds to milliseconds. This sequence is often called a spin echo. This sequence is used to avoid dead time of the NMR electronics in receiving the signal.

In characterizing petroleum (also referred herein as "oil" or "hydrocarbons"), there are two types of relaxation processes commonly used: T1 and T2. T1 refers to the spin-lattice relaxation time and is often measured by an inversion recovery method or a saturation recovery method. T2 refers to a spin-spin relaxation time and is often considered a preferable measurement due to the ability to obtain the measurement more quickly. With respect to T1, inversion recovery is often measured by the following sequence: $\pi$-$\tau$-$\pi/2$-FID acquisition.

The initial $\pi$ pulse inverts the magnetization, and the subsequent measurement of FID signal as a function of $\tau$ allows the determination of the recovery curve which may then be fitted to relaxation model or be subject to Laplace inversion to obtain the T1 spectrum. The acquisition part of the sequence can also be replaced by the spin-echo detection as previously mentioned.

The measurement of T2 is often performed utilizing the CPMG (Carr-Purcell-Meiboom-Gill) pulse sequence: $\pi$-te/

2-π-{te(ACQ)-π}$_N$ where the bracketed sequence is repeated N times (and a time period T2=N*te), and an echo signal is recorded for every echo time period te. Signal acquisition is performed in between every adjacent π pulse pair. A CPMG pulse sequence is often performed with a long train of π pulses and produces many echoes such that a determination of T2 can be quickly obtained. The resulting echo signals can be analyzed by relaxation models or Laplace inversion to obtain a T2 spectrum.

In one aspect, NMR relaxation and spectroscopy pulse sequences and processing are combined to obtain information about a sample. In one embodiment, a pulse sequence seen in FIG. 1a and described by π/2-τ1-π/2-Δ-CPMG is utilized, where π/2 represents a ninety degree pulse, τ1 is a spectroscopy time period that is incremented multiple times during an experiment, Δ is a fixed period of time, and CPMG is a Carr-Purcell-Meiboom-Gill pulse sequence utilizing a second time period τ2, which is incremented multiple times during the experiment. τ2 is equal to N*te. In various embodiments, time period T2 is incremented multiple times for each τ1 increment. For purposes herein, an "experiment" is to be understood broadly to involve subjecting a sample to a pulse sequence a plurality of times and where at least one time between pulses of the pulse sequence is varied. The combined sequence can be viewed as having a first portion (before the Δ) that is the spectroscopy portion of the sequence, and a second portion (CPMG) that is the relaxation portion of the sequence. More particularly, the first part of the pulse sequence, π/2-τ1-π/2, is the spectroscopy portion of the pulse sequence. The precession of molecules is initiated by the first π/2 pulse, and it is allowed to proceed for the time τ1. At the end of the τ1 period, the second π/2 pulse is applied to rotate the transverse magnetization back to a longitudinal direction thus stopping the precession. The longitudinal direction may be the direction of the magnetic field $B_0$. This precession is stopped by the second π/2 pulse to rotate the transverse magnetization to the longitudinal direction (z). The magnetization (m) that is stored along the z-direction can be written as m(τ1)=$m_0$ cos($\chi$*τ1*$\omega_0$+$\phi$), where $m_0$ is the total signal with the chemical shift $\chi$ which is proportional to the amount of the corresponding molecular species, and $\phi$ is the relative phase angle between the two π/2 pulses. For example, if $\phi$=0°, then the signal is cosine modulated, whereas if $\phi$=90°, then the signal is sine modulated. It is conventional to use both cosine and sine data to achieve the maximum width of the frequency spectrum. However, it is also possible to use only cosine or sine data where the useable frequency spectrum is reduced.

The data in such an experiment can be written in a matrix format because the data is acquired with two independent parameters, τ1 and τ2; m(τ1,τ2). The size of the first dimension is number of τ1 used in the experiment, and the size of second dimension corresponds to the total number of echoes, N.

Assuming several molecular species are present in the sample, the acquired signal can be written according to above equation (1):

$$M(\tau1, \tau2) = \int f(\chi, T2)\cos(\chi*\tau1*\omega)e^{(-\frac{\tau2}{T2})}d\chi dT2,$$

where $f$ is a distribution function proportional to the density of spins with the specific chemical shift $\chi$ and spin-spin relaxation time T2. Integration ranges are the allowed range of frequency $\chi$ and that of T2. Signal-to-noise ratios may be improved by integrating the peaks along the frequency dimension before performing a Laplace inversion as discussed hereinafter.

Figure 1B:
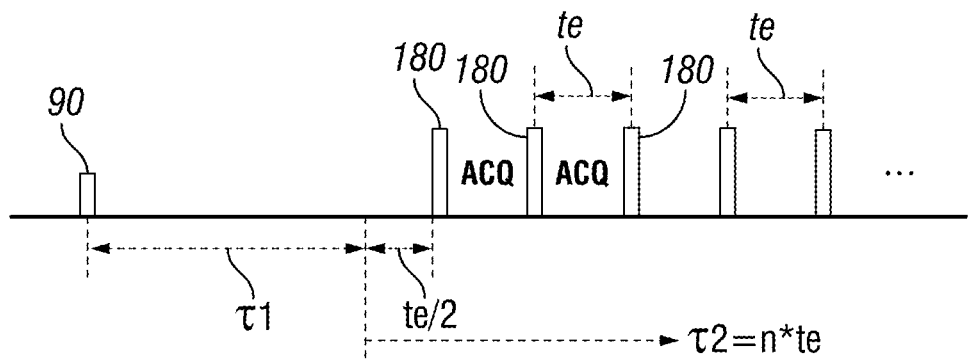
FIG. 1b is a schematic of a modified first T2 plus spectroscopy combined pulse sequence.

If desired, the combined pulse sequence of FIG. 1a can be modified (shortened) as shown in FIG. 1b and described by π/2-τ1-te/2-{η-te(ACQ)}$_N$, where π represents a hundred-eighty degree pulse, π/2 represents a ninety degree pulse, τ1 is a spectroscopy time period that is incremented multiple times during an experiment, it represents a hundred-eighty degree pulse, to is an echo time, te(ACQ) refers to signal acquisition during the echo time, and N is a number of repetitions that is incremented multiple times during the experiment. In this case, the spectroscopy portion of the signal is reduced to π/2-τ1 and the CPMG sequence utilizes the spectroscopy portion as the beginning of its sequence. As with the sequence of FIG. 1a, in an experiment this sequence is repeated for multiple τ1 values, and for each τ1 value, the CPMG portion of the sequence is run with multiple τ2 values. The acquired signal is the same as set forth with respect to the pulse sequence of FIG. 1a (e.g., the signal written according to equation (1)).

Figure 2:
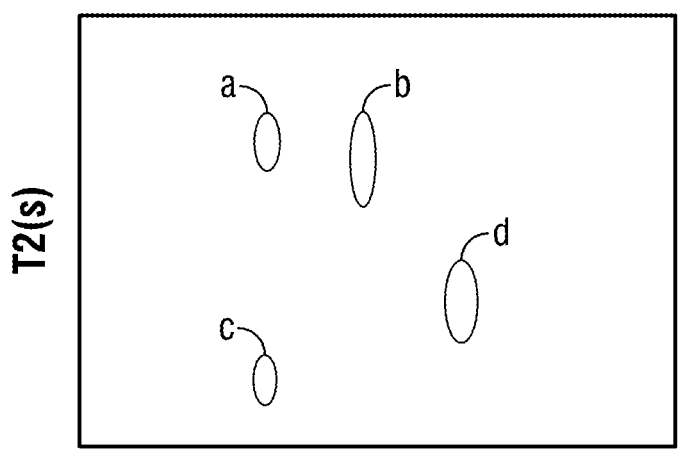
FIG. 2 is a schematic of a hypothetical two-dimensional spectrum obtained from processing a signal obtained as a result of the first T2 plus spectroscopy combined pulse sequence.

As described hereinafter with respect to FIG. 11a, in one embodiment, data analysis on the received signal M(τ1,τ2) is performed by conducting a Fourier transform along the τ1 direction and then a Laplace inversion along the τ2 direction, thereby generating a two-dimensional spectrum with peaks identifying different molecules present in the sample. An example of a hypothetical resulting two-dimensional spectrum is seen in FIG. 2 where four components (labeled a-d) of a sample are plotted on a graph utilizing chemical shift (ppm) as the x-axis and relaxation time T2 as the y-axis. In FIG. 2, the ovals represent peaks of four hypothetical components. It will be appreciated that signals for components "a" and "b" share a similar T2 value so they would overlap in a T2 experiment and the quantity (or existence) of each might be undetermined. Similarly, signals for components "a" and "c" share a similar chemical shift such that they would overlap in an NMR spectroscopy experiment and the quantity (or existence) of each might be undetermined. However, by utilizing a combined relaxation-spectroscopy pulse sequence and appropriately processing the received data, (i) signals from molecules with the same chemical shift but different T2 times and (ii) signals from molecules with the same T2 times but different chemical shifts are all separated.

According to one embodiment, an integration of the signal under a region around a peak can provide the total signal attributed to the respective peak, and thus its weight percentage in the sample.

Figure 3:
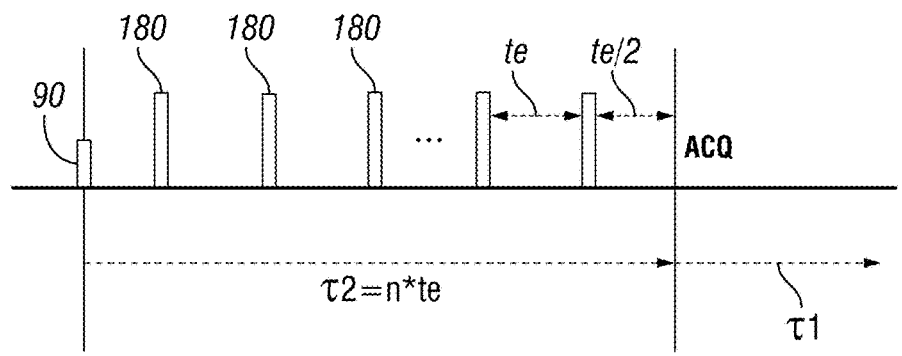
FIG. 3 is a schematic of a second T2 plus spectroscopy combined pulse sequence that reverses the order of the modified first combined pulse sequence of FIG. 1b.
Figure 4A:
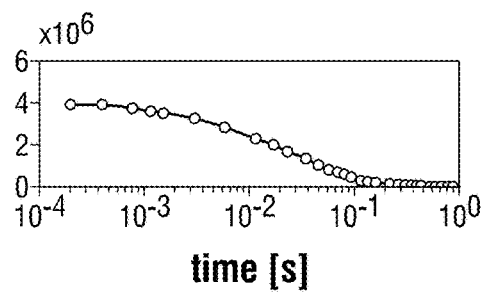
FIGS. 4a-4d are the relaxation decay, relaxation time distribution, relaxation decay of the largest peak in the spectrum and the associated distribution of relaxation times of an oil sample obtained from partial processing of a signal obtained utilizing the combined pulse sequence of FIG. 3.
Figure 4B:
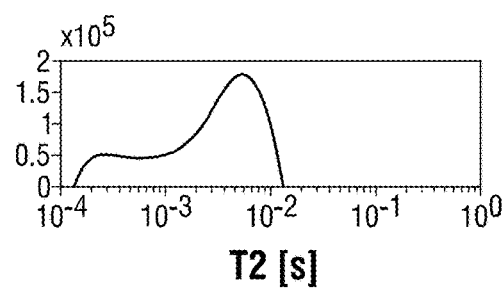
Figure 4C:
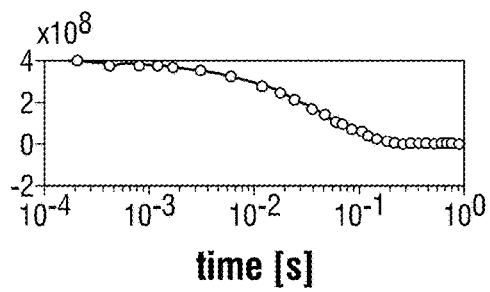
Figure 4D:
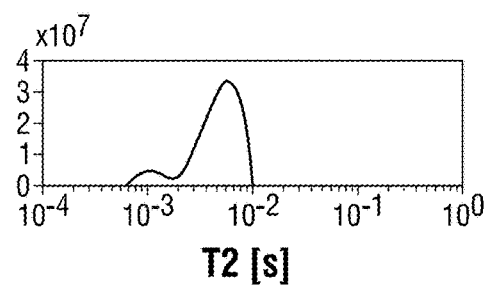

Turning now to FIG. 3, a combined spectroscopy and relaxation pulse sequence is shown where the sequence order is reversed relative to the sequences shown in FIGS. 1a and 1b such that the CPMG sequence is followed by a spectroscopy acquisition (e.g., CPMG-ACQ). The sequence shown in FIG. 3 may be described by π/2-{te-η}$_N$-te/2-τ1 (ACQ), where π/2 represents a ninety degree pulse, te is an echo time, π represents a hundred-eighty degree pulse, N is a number of repetitions that is incremented multiple times during an experiment, τ1 is a spectroscopy time period that is incremented multiple times during an experiment, and τ1(ACQ) refers to acquisition of a spectroscopy signal during the spectroscopy time period. In this sequence, the spectroscopy portion is based on the free induction decay occurring after the last echo of the CPMG sequence. Data analysis for the resulting detected signal is performed in the same manner as with the sequences of FIGS. 1a and 1b with a Fourier transform along the τ1 direction and then a Laplace inversion along the τ2 direction thereby generating a two-dimensional spectrum with peaks identifying different molecules present in the sample.

An experiment on a plurality of different oils utilizing the pulse sequence of FIG. 3 was conducted. The number of echoes was increased in approximately logarithmic fashion to cover the complete decay of the signal with the longest relaxation time T2 by incrementing the number N of echoes appropriately from scan to scan while acquiring data. In the specific experiment, the maximum τ1 was 0.5 seconds, the maximum T2 was 1 second, the dwell time was 20 μs, the number of T2 values was 32, the echo time to was 200 μs, the π/2 pulse length t90 was 6.5 μs, and the π pulse length t180 was 13.0 μs. Data were processed by Fourier transformation over τ1, phase correction, baseline correction, and then Laplace inversion over τ2.

Figure 5A:
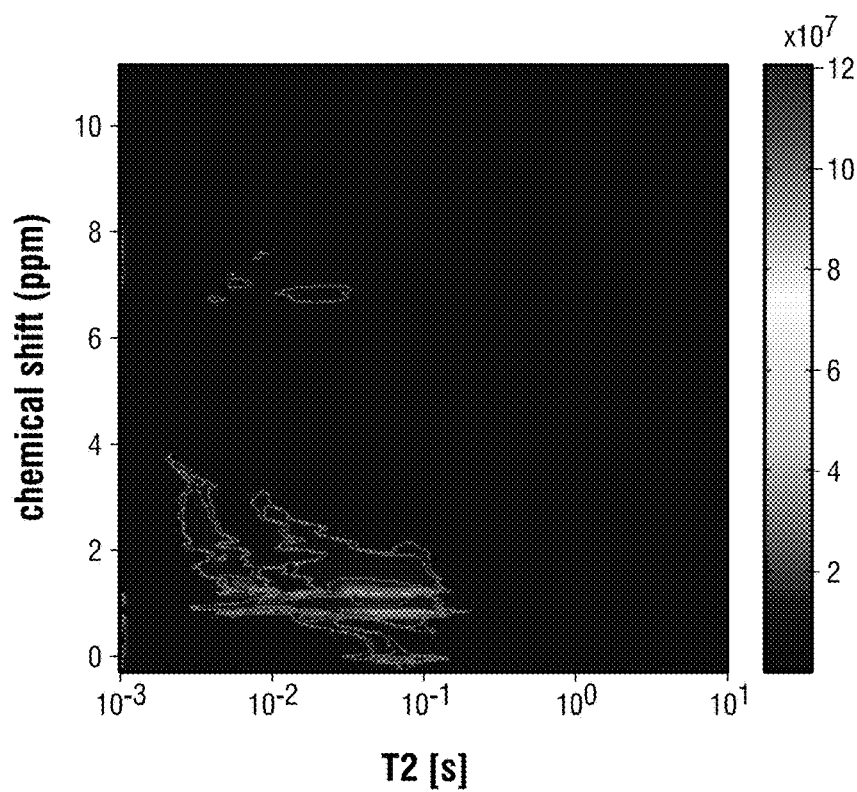
FIG. 5a is a two-dimensional spectrum geography map showing the distribution of relaxation times for each chemical shift for the oil sample used with respect to FIGS. 4a-4d and resulting after complete processing of a signal obtained utilizing the combined pulse sequence of FIG. 3.
Figure 5B:
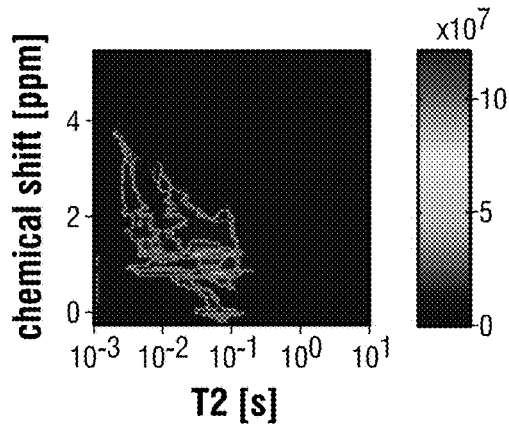
Figure 5C:
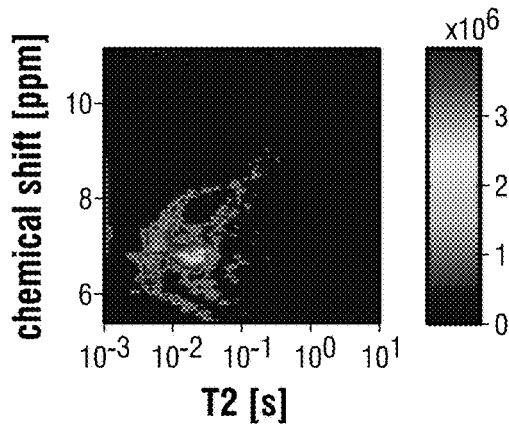
Figure 6A:
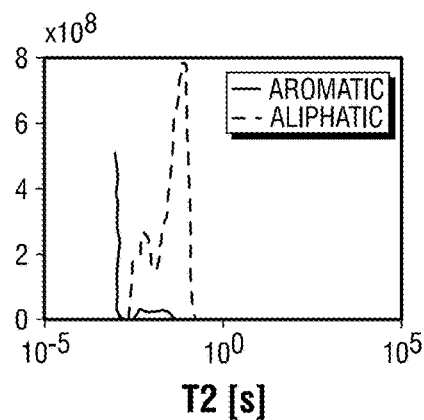
Figure 6B:
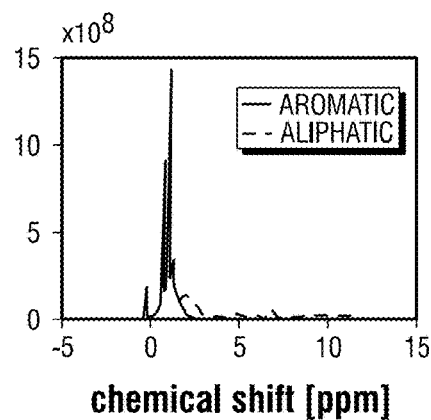
Figure 7A:
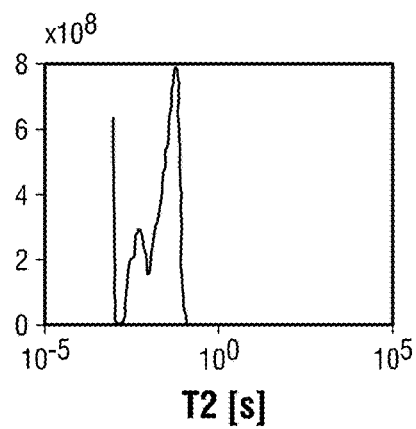
Figure 7B:
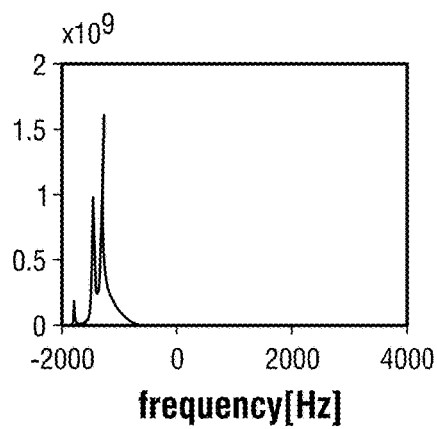

Shown in FIGS. 4a-4d are respectively the relaxation decay, relaxation time distribution, relaxation decay of the largest peak in the spectrum and the associated distribution of relaxation times for a first oil ("Oil 11"), calculated by processing the obtained signal via Fourier transformation over τ1, phase correction, and baseline correction without Laplace inversion. The two-dimensional spectrum showing the distribution of relaxation times for each chemical shift resulting after Laplace inversion over τ2 can be shown in different fashions, such as contour plots and 3D-type geography maps which provide indications of amplitude for each element of the sample. A geography map is seen in FIG. 5a. The aliphatic and aromatic regions of FIG. 5a are shown respectively in FIGS. 5b and 5c, and projections along the chemical shift and T2 dimensions for selected regions illustrating achievable selectivity are shown in FIGS. 6a and 6b. Non-selective projections of the two-dimensional spectrum of FIG. 5a along the frequency and T2 dimensions are seen in FIGS. 7a and 7b.

The relaxation time distributions of the multiple oils tested (only Oil 11 being shown) revealed different signatures for the aromatic and the aliphatic resonances. For certain oils, nearly all aromatic signals relax rapidly, while for other oils, aromatics relax slowly. The former oils (rapid relaxation) are the ones that contain appreciable amounts of asphaltene (between 3 and 12.9 wt %) while the asphaltene content of the latter (slow relaxation) is very small to zero (≤0.1 wt %). This indicates that asphaltene functions as a relaxation agent for the aromatic components in crude oil.

According to one aspect, this result shows that the aromatic molecules are more sensitive to the presence of the asphaltenes in comparison to the presence of the non-aromatic hydrocarbons. Thus, the measurement of the relaxation rates (T2 and T1) of aromatic protons can be used as a sensitivity probe of the presence and concentration of asphaltenes in the crude oil. The method described here allows the selection of the aromatic protons and the determination of their relaxation rates and thus can be used to detect asphaltenes.

Figure 8:
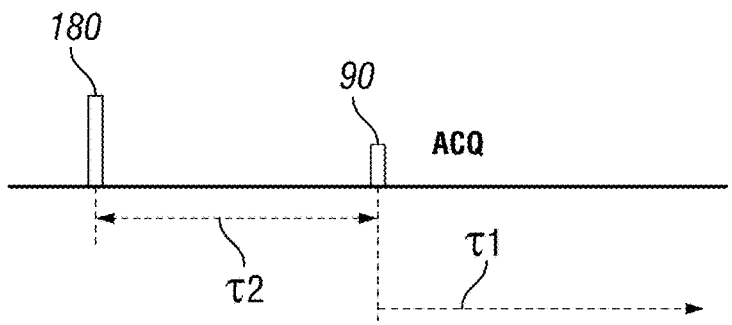
FIG. 8 is a schematic of a T1 plus spectroscopy combined pulse sequence.

While the combined pulse sequences of FIGS. 1a, 1b, and 3 are directed to a combination of NMR spectroscopy and NMR T2 relaxation, a combined pulse sequence of spectroscopy and T1 relaxation is also possible. In one embodiment, NMR spectroscopy and T1 relaxation are combined according to a pulse sequence shown in FIG. 8 which may be described by π-τ2-π/2-τ1(ACQ), where π is a hundred-eighty degree pulse, τ2 is a time period that is incremented multiple times during an experiment, π/2 is a ninety degree pulse, τ1 is a spectroscopy time period that is incremented multiple times during the experiment, and τ1(ACQ) refers to acquisition of a spectroscopy signal during the spectroscopy time period. In this case, the first portion of the signal corresponds to the T1 relaxation pulse sequence, and the acquisition portion corresponding to the NMR spectroscopy pulse sequence. Assuming several molecular species are present in the sample, the acquired signal can be written according to:

$$M(\tau1, \tau2) = \int f(\chi, T1)\cos(\chi*\tau1*\omega)[1 - 2e^{(-\frac{\tau2}{T1})}]d\chi dT1, \quad (4)$$

where $f$ is a distribution function proportional to the density of spins with the specific chemical shift $\chi$ and spin-lattice relaxation time T1. Integration ranges are the allowed range of frequency $\chi$ and that of T1. As described hereinafter with respect to FIG. 11a, in one embodiment, data analysis on the received signal M(τ1,τ2) is performed by conducting a Fourier transform along the τ1 direction and then a Laplace inversion along the τ2 direction, thereby generating a two-dimensional spectrum with peaks identifying different molecules present in the sample.

Figure 9:
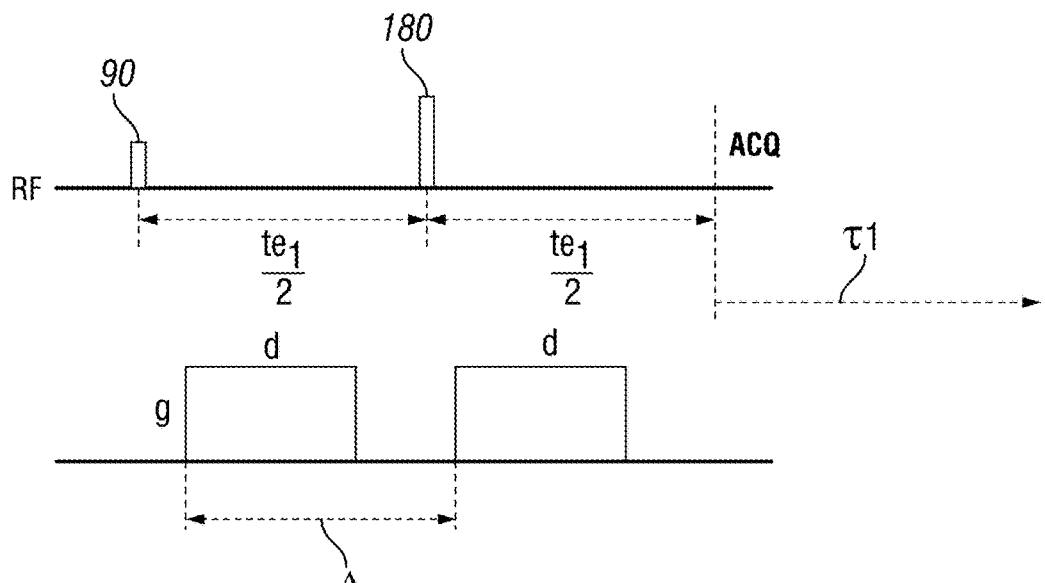
FIG. 9 is a schematic of a D plus spectroscopy combined pulse sequence.

FIG. 9 is a schematic of a pulse sequence with NMR diffusion (D) plus spectroscopy, which can be described by π/2-te$_1$/2-π-te$_1$/2-τ1(ACQ), where te$_1$ is an echo time, τ1 is a spectroscopy time period that is incremented multiple times during the experiment, and τ1(ACQ) refers to acquisition of a spectroscopy signal during the spectroscopy time period where the NMR system receives signals resulting from precessing spins. A first field gradient pulse is applied during a first time period te$_1$/2 and a second field gradient pulse is applied during a second time period te$_1$/2. The first field gradient pulse and second field gradient pulse have equal durations (d) and amplitudes (g). The amplitudes (g) are incremented multiple times during the experiment. Assuming the diffusion constant of a molecule is D, then the acquired signal can be expressed according to equation (2): M(b,τ1)=∫∫f(χ,D)cos(χ*τ1*ω)e$^{-b*D}$dχdD, where $$b = \gamma^2 g^2 d^2 \left(\Delta - \frac{d}{3}\right),$$

Δ is the time delay between the rising edge of the two gradient pulses, γ is the gyromagnetic ratio of the nuclei. The measurement is performed for several different b values that can be obtained by changing one or more of duration d, time delay Δ, and amplitude g.

Data analysis for the data obtained as a result of the diffusion plus spectroscopy combined pulse sequence is performed by conducting a Fourier transform along the τ1 direction and then a Laplace inversion along the b direction thereby generating a two-dimensional spectrum with peaks identifying different molecules present in the sample. The two-dimensional spectrum is optionally plotted on a graph utilizing chemical shift (ppm) as one axis and diffusion D as the other axis, thereby separating signals from molecules with the same chemical shift but different D's and signals from molecules with the same D's but different chemical shifts. An integration of the signal under a region around a peak provides the total signal attributed to the respective peak, and thus its weight. This type of experiment is commonly known as Diffusion Ordered Spectroscopy (DOSY).

Figure 10:
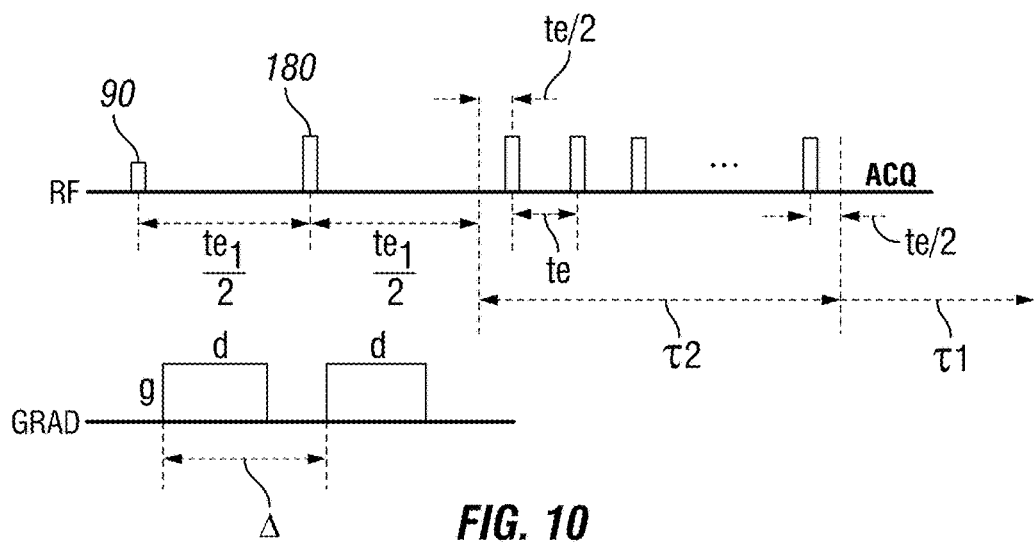
FIG. 10 is a schematic of a T2 plus D plus spectroscopy combined three-dimensional pulse sequence.

FIG. 10 is a schematic of a combined three dimensional pulse sequence with T2 plus D plus spectroscopy. The sequence can be described by π/2-te$_1$/2-π-te$_1$/2-te/2-{π- te$\}_N$-te/2-$\tau$1(ACQ), where $\pi/2$ is a ninety degree pulse, te$_1$ is a first echo time, $\pi$ is a hundred-eighty degree pulse, te is a second echo time, N is a number of repetitions that is incremented multiple times during an experiment, $\tau$1 is a spectroscopy time period that is incremented multiple times during the experiment, and $\tau$1(ACQ) refers to acquisition of a spectroscopy signal during the spectroscopy time period. In this case, the NMR diffusion (D) plus spectroscopy pulse sequence described above with respect to FIG. 9 is modified to include a CPMG sequence after the first two pulses and before the acquisition $\tau$1(ACQ). Note that te$_1$ is the echo time for the first spin echo segment, and te is the echo time for the CPMG segment. Again, field gradient pulses of equal duration d and amplitude g are applied during each of the te$_1$/2 periods. The amplitudes (g) are incremented multiple times during the experiment. In one embodiment, $\tau$1 is incremented for each increment of N and, in turn, N is incremented for each increment of g. The acquired signal M can be expressed according to the equation $$M(\tau 1, \tau 2, b) = \int f(\chi, T1)\cos(\chi * \tau 1 * \omega) e^{(-b*D)} e^{\left(-\frac{\tau 2}{T2}\right)} d\chi dT2 dD, \quad (5)$$

where $f$ is a distribution function proportional to the density of spins with the specific chemical shift $\chi$, spin-spin relaxation time T2 and diffusion constant D. Integration ranges are an allowed range of frequency $\chi$ and that of T2 and diffusion constant D. Similar to the procedure described hereinafter with respect to FIG. 11*a* for the 2D data set, in some embodiments, data analysis on the received signal M($\tau$1,$\tau$2,b) is performed by conducting a Fourier transform along the $\tau$1 direction and then a 2D Laplace inversion along the $\tau$2 and b directions simultaneously, thereby generating a three-dimensional spectrum. An example of a 2D Laplace inversion is described in U.S. Pat. No. 6,462,542 issued on Oct. 8, 2002, which is incorporated by reference herein in its entirety. The inversion of the b and $\tau$2 dimension can also be done in two steps by, for example, performing Laplace inversion along $\tau$2 first and then along b. The three-dimensional spectrum may be plotted on a graph utilizing chemical shift (ppm) as one axis, diffusion D as another axis, and T2 as a third axis, thereby separating signals from molecules having at least one different value along one of the axes. An integration of the signal under a region around a peak provides the total signal attributed to the respective peak, and thus its weight.

According to another embodiment, a combined three dimensional pulse sequence with NMR T1 plus D plus spectroscopy can be utilized. According to a further embodiment, a combined three dimensional pulse sequence with NMR T1 plus T2 plus spectroscopy can be utilized.

Figure 11A:
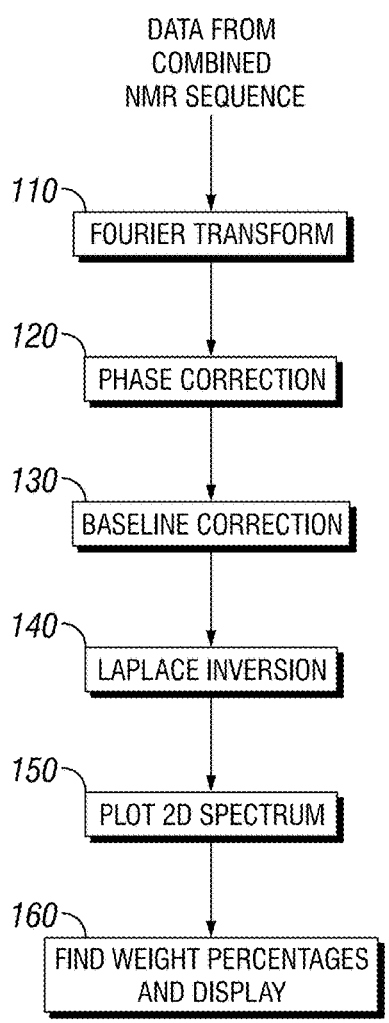
FIG. 11a is a flow chart of a method of processing data obtained as a result of a combined NMR pulse sequence in order to characterize fluid.

FIG. 11*a* is a flow chart of one method of processing data obtained as a result of a combined NMR T2 plus spectroscopy combined pulse sequence such as shown in FIGS. 1*a*, 1*b*, and 3, in order to characterize fluid. At 110, the data resulting from the combined NMR pulse sequence is Fourier transformed over $\tau$1. At 120, the Fourier transformed data is optionally subjected to phase correction, and at 130, the phase corrected data is optionally subjected to baseline correction. At 140, the optionally phase and baseline corrected data is subject to a Laplace inversion over T2 in order to obtain a two-dimensional spectrum. If desired, the two-dimensional spectrum may be plotted for viewing on paper or an electronic medium at 150 with particular areas on the graph corresponding to particular molecules or groups of molecules, thereby characterizing the fluid. The axes of the graph may be chemical shift and T2 relaxation. Alternatively or additionally, at 160 the areas under the "peaks" identified in the two-dimensional spectrum may be assessed (e.g., via integration) to obtain weight percentage values for one or more of the molecule-types or molecule-groups in the sample. For example, weight percentage values may be obtained to characterize the fluid for each of water, $CH_2$, $CH_3$, $CH_4$, ethane, etc. to the extent that they are present in the sample. As another example, weight percentage values may be obtained for aromatic and aliphatic groups alone or in addition to water, $CH_2$, $CH_3$, etc. The weight percentages may be displayed on paper or electronic medium in any of many forms including a table, a bar graph, or otherwise, thereby characterizing the fluid.

In another embodiment, rather than first conducting a Fourier transform over $\tau$1 and a Laplace transform over $\tau$2, a Laplace transform is first performed in the second direction ($\tau$2) followed by a Fourier transform in the first direction ($\tau$1).

In another embodiment, a method of processing data obtained as a result of a combined NMR D plus spectroscopy combined pulse sequence, such as shown in FIG. 9, includes a Fourier transform along the $\tau$1 direction and then a Laplace inversion along the b direction thereby generating a two-dimensional spectrum with peaks identifying different molecules present in the sample. Phase and baseline correction may also be utilized between the Fourier transform and Laplace inversion. The two-dimensional spectrum is optionally plotted on a graph utilizing chemical shift as one axis and diffusion D as the other axis, thereby characterizing the fluid. Alternatively or additionally, the areas under the "peaks" identified in the two-dimensional spectrum may be assessed (e.g., via integration) to obtain weight percentage values for one or more of the molecule-types or molecule-groups in the sample. The weight percentages may be displayed on paper or electronic medium in any of many forms including a table, a bar graph, or otherwise, thereby characterizing the fluid.

Similar techniques may be used for combined pulse sequences generating data from which a two-dimensional spectrum may be obtained. Likewise, similar techniques may be used for combined pulse sequences generating data from which a three-dimensional spectrum may be obtained and used to characterize the fluid.

Figure 11B:
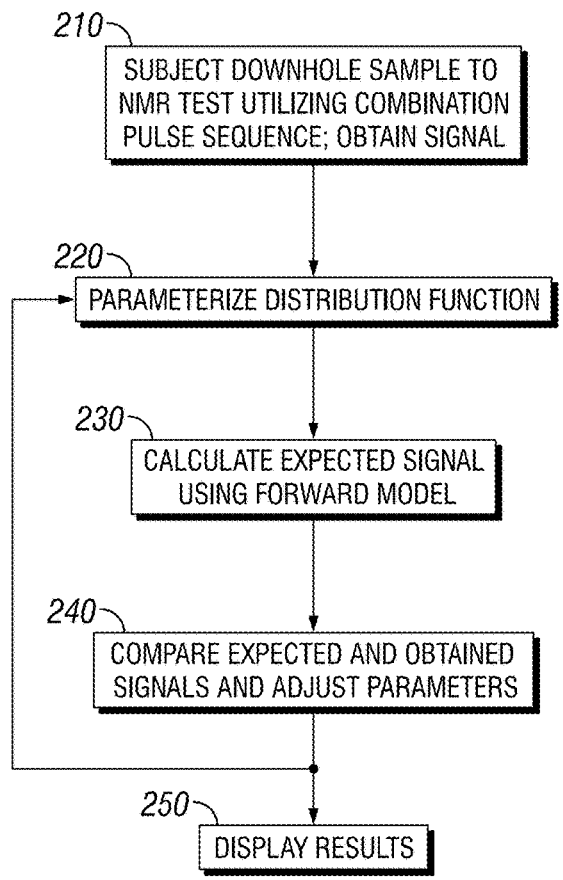
FIG. 11b is a flow chart of a second method for characterizing fluid utilizing a combined NMR pulse sequence.

Another method for characterizing the fluid is seen in FIG. 11*b*. At 210, a downhole sample is subjected to an NMR test utilizing a combination pulse sequence in order to obtain a measured signal (actual data). The combination pulse sequence may be any of the previously described pulse sequences or another pulse sequence combining spectroscopy and NMR relaxation or diffusion. At 220, a distribution function is parameterized in terms of a plurality of parameters, such as one peak for water, one for each of $CH_2$, $CH_3$, $CH_4$ (methane), ethane, etc. Each peak is characterized by a chemical shift, and one or more of a relaxation or diffusion, and an amplitude. At 230, using a forward model related to the combination pulse sequence utilized downhole, an expected signal is calculated for a particular combination of molecules (expected sample). The particular combination of molecules expected may be based on no information, some information, or considerable information. For example, if an optical test on the sample was previously run, some information regarding the sample might be available. Or, if actual samples of fluids from the formation were previously obtained (e.g., by a formation tester apparatus) and analyzed at the surface, considerable information may be available. At 240, the expected signal is compared to the actual data, and the parameters (e.g., one or more of the amplitudes, the relaxation times and peak widths) are adjusted (e.g., using a multi-dimensional search) in an iterative search (repeating 220, 230, 240) until the expected signal generated from the model is consistent with the measured data, or until a best fit is found. The results may be displayed in any desired manner such as by two-dimensional graph, chart, bar graph, etc., on paper or electronically.

According to one aspect, the NMR pulse sequences that includes both NMR spectroscopy and at least one of NMR relaxation and diffusion techniques are carried out by a downhole NMR tool, and the signals obtained are obtained by a downhole NMR tool. Processing may be accomplished downhole or uphole.

Figure 12:
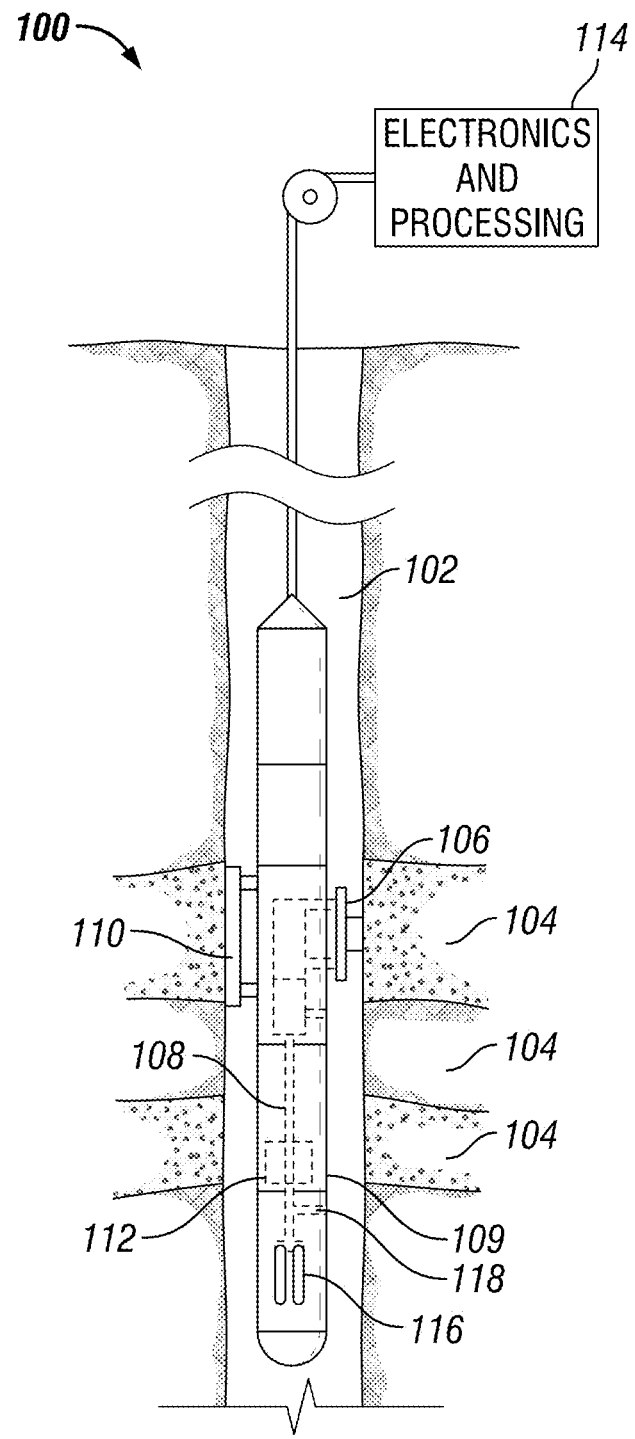
FIG. 12 is a schematic diagram of an apparatus for characterizing hydrocarbon samples.

Turning to FIG. 12, a schematic diagram shows a wellbore tool 100 for characterizing hydrocarbon samples. In this example, the wellbore tool 100 is a wireline tool. The wireline tool 100 is disposed within a wellbore 102 that traverses a formation 104. The wireline tool includes 100 a formation fluid testing module, such as the Modular Formation Dynamics Tester™ (MDT) module of Schlumberger. The formation fluid testing module includes a selectively extendable fluid admitting assembly (e.g., probe) 106. This assembly 106 extends into the formation 104 and withdraws formation fluid from the formation 104 (e.g., samples the formation). The fluid flows through the assembly 106 and into a flow line 108 within a housing 109 of the tool 100. A pump module (not shown) is used to withdraw the formation fluid from the formation 104 and pass the fluid through the flow line 108. An optical analyzer (not shown) can be used to conduct optical tests on the fluid within the flow line 108. The wireline tool 102 may also include a selectively extendable tool anchoring member 110 that is arranged to press the probe 106 assembly against the formation 104.

The wireline tool 100 also includes a NMR system 112 for analyzing at least a portion of the fluid in the flow line 108 (e.g., an oil sample). In illustrative embodiments, the NMR system 112 uses a magnet to apply a homogeneous static magnetic field to the fluid in the flow line 108. The NMR system also includes an NMR transmitter coupled to a coil. The NMR transmitter generates a pulse sequence that incorporates a combination of NMR spectroscopy and relaxation techniques and the coil applies them to the fluid in the flow line 108. The NMR signals generated by the sequences within the fluid are then detected using the coil and an NMR receiver. Those detected signals can then be interpreted and analyzed by a processing system 114. In this manner, the NMR system 112 performs an NMR analysis of the fluid within the flow line 108 to obtain a two-dimensional or three-dimensional spectrum. Further details regarding downhole NMR systems that can perform NMR analysis in a flow line can be found in U.S. Pat. No. 8,471,559, issued on Jun. 25, 2013, and U.S. Patent Application Publication No. 2012/0169334, published on Jul. 5, 2012. Each of these references is incorporated by reference herein in their entireties.

The processing system 114 may be located uphole and signals may be sent from the wireline tool 100 uphole for processing. Display elements (electronic and/or print) may be located with the uphole processing system or may be located elsewhere. The processing system can be used for generating a two-dimensional or three-dimensional spectrum from the detected signals and analyzing the spectrum, as described herein. In some embodiments, the wireline tool 100 may contain a processing system. The processing system may be used to analyze the NMR data obtained by the NMR receiver 112 in order to determine the concentration of contamination of the sample.

The term "processing system" should not be construed to limit the embodiments disclosed herein to any particular device type or system. The processing system may be a computer, such as a laptop computer, a desktop computer, or a mainframe computer. The processing system may include a graphical user interface (GUI) so that a user can interact with the processing system. The processing system may also include a processor (e.g., a microprocessor, microcontroller, digital signal processor, or general purpose computer) for executing any of the methods and processes described above. The processing system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The memory can be used to store computer instructions (e.g., computer program code) that are interpreted and executed by a processor.

The NMR pulse sequences described herein may be implemented as a series of computer instructions (e.g., software or firmware) fixed on a non-transitory tangible medium, such as a computer readable medium (e.g., a memory), or transmittable to the computer system, via a modem or other interface device, such as a communications adapter connected to a network over a tangible medium (e.g., optical or analog communications lines). The series of computer instructions can embody all or part of the NMR pulse sequences. A processor may be configured to retrieve the sequences from memory and provide instructions to the NMR transmitter to apply the sequences to a substance. The detected resonant signals may also be communicated from the NMR receiver to a processor for storage on memory.

After the NMR system 112, the formation fluid (e.g., the oil sample) may be pumped out of the flow line 108 and into the wellbore 102 through a port 118. Some of the formation fluid may also be passed to a fluid collection module 116 that includes chambers for collecting fluid samples and retaining samples of the formation fluid for subsequent transport and testing at the surface (e.g., at a testing facility or laboratory).

The methods described herein can be implemented by various other wellbore tools and wellbore tool configurations. For example, the methods described herein can be implemented by a wellbore tool that is conveyed by other means, such coiled tubing. Furthermore, the methods described herein can also be applied in logging-while-drilling (LWD) operations, sampling-while-drilling operations, measuring-while-drilling operations, or any other operation where monitoring of formation fluid is performed.

Furthermore, in some embodiments, the methods described herein are performed in a wellbore using a wellbore tool. In other embodiments, the methods described herein are performed at the surface using a laboratory NMR system on formation fluid that has been brought to the surface. Also, the methods described herein can be used to analyze a variety of different types of formation fluids. In particular, the methods can be used to analyze light oils, heavy oils, biodegraded oils, water washed oils, live oils, dead oils, gases, and water.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

We claim:

1. A method for characterizing a sample containing a plurality of molecular species, the method comprising:
   subjecting the sample to a nuclear magnetic resonance (NMR) field according to an NMR pulse sequence that includes (i) an NMR spectroscopy portion and (ii) an NMR spin-spin T2 relaxation time portion, where said pulse sequence is $\pi/2$-$\tau 1$-$\pi/2$-$\Delta$-CPMG, where $\pi/2$ represents a ninety degree pulse, $\tau 1$ is a spectroscopy time period that is incremented multiple times during an experiment, $\Delta$ is a fixed period of time, and CPMG is a Carr-Purcell-Meiboom-Gill pulse sequence utilizing a second time period $\tau 2$, which is incremented multiple times during the experiment;
   measuring a measured signal resulting from an interaction of said NMR field according to said NMR pulse sequence and the sample;
   processing the measured signal using a first transform over a spectroscopy variable and using a second transform over an NMR relaxation variable to obtain a multi-dimensional spectrum; and
   using the multi-dimensional spectrum to characterize the sample.

2. A method according to claim 1, wherein:
   said first transform is a Fourier transform and said second transform is a Laplace inversion, and said processing comprises Fourier transforming said obtained signal over $\tau 1$ and Laplace inverting said Fourier transformed signal over $\tau 2$ in order to obtain said multi-dimensional spectrum.

3. A method according to claim 2, wherein:
   said processing further comprises phase correcting and baseline correcting said Fourier transformed signal prior to said Laplace inverting.

4. A method according to claim 2, wherein:
   said using comprises displaying said multi-dimensional spectrum as a graph with chemical shift as one axis and T2 relaxation time as another axis.

5. A method according to claim 2, wherein:
   said using comprises obtaining weight percentages of at least a plurality of molecular species from said multi-dimensional spectrum, and displaying an indication of said weight percentages.

6. A method according to claim 1, wherein:
   said first transform is a Fourier transform and said second transform is a Laplace inversion, and said processing comprises Laplace inverting said obtained signal over $\tau 2$ and then Fourier transforming said Laplace inverted signal over $\tau 1$ to obtain said multi-dimensional spectrum.

7. A method according to claim 1, wherein the sample is a hydrocarbon sample.

8. A method according to claim 7, wherein:
   said using comprises determining relaxation rates of aromatic protons, and from said relaxation rates, determining the presence of asphaltenes in said hydrocarbon sample.

9. A method according to claim 8, wherein:
   said using further comprises determining a concentration of asphaltenes in said hydrocarbon sample based on said relaxation rates of said aromatic protons.

10. A method for characterizing a sample containing a plurality of molecular species, the method comprising:
    subjecting the sample to a nuclear magnetic resonance (NMR) field according to an NMR pulse sequence that includes (i) an NMR spectroscopy portion and (ii) an NMR relaxation portion where said pulse sequence is $\pi/2$-$\tau 1$-te/2-$\{\pi$-te(ACQ)$\}_N$, where $\pi$ represents a hundred-eighty degree pulse, $\pi/2$ represents a ninety degree pulse, $\tau 1$ is a spectroscopy time period that is incremented multiple times during an experiment, $\pi$ represents a hundred-eighty degree pulse, te is an echo time, te(ACQ) refers to signal acquisition during the echo time, and N is a number of repetitions that is incremented multiple times during the experiment;
    measuring a measured signal resulting from an interaction of said NMR field according to said NMR pulse sequence and the sample;
    processing the measured signal using a first transform over a spectroscopy variable and using a second transform over an NMR relaxation variable to obtain a multi-dimensional spectrum; and
    using the multi-dimensional spectrum to characterize the sample.

11. A method according to claim 10, wherein:
    said first transform is a Fourier transform and said second transform is a Laplace inversion, and said processing comprises Fourier transforming said obtained signal over $\tau 1$ and Laplace inverting said Fourier transformed signal over $\tau 2$ in order to obtain said multi-dimensional spectrum, where $\tau 2$ is equal to N*te.

12. A method according to claim 11, wherein:
    said using comprises displaying said multi-dimensional spectrum as a graph with chemical shift as one axis and T2 relaxation time as another axis.

13. A method according to claim 10, wherein:
    said using comprises obtaining weight percentages of a plurality of molecular species from said multi-dimensional spectrum and displaying an indication of said weight percentages.

14. A method according to claim 10, wherein the sample is a hydrocarbon sample.

15. A method according to claim 14, wherein:
    said using comprises determining relaxation rates of aromatic protons, and from said relaxation rates, determining the presence of asphaltenes in said hydrocarbon sample.

16. A method according to claim 15, wherein:
    said using further comprises determining a concentration of asphaltenes in said hydrocarbon sample based on said relaxation rates of said aromatic protons.

17. A method comprising:
    subjecting a sample to a nuclear magnetic resonance (NMR) field according to an NMR pulse sequence that includes (i) an NMR spectroscopy portion and (ii) an NMR relaxation portion where said pulse sequence is $\pi/2$-$\{$te-$\pi\}_N$-te/2-$\tau 1$(ACQ), where $\pi/2$ represents a ninety degree pulse, te is an echo time, π represents a hundred-eighty degree pulse, N is a number of repetitions that is incremented multiple times during an experiment, τ1 is a spectroscopy time period that is incremented multiple times during an experiment, and τ1(ACQ) refers to acquisition of a spectroscopy signal during the spectroscopy time period;

measuring a measured signal resulting from an interaction of said NMR field according to said NMR pulse sequence and the sample;

processing the measured signal using a first transform over a spectroscopy variable and using a second transform over an NMR relaxation variable to obtain a multi-dimensional spectrum; and using the multi-dimensional spectrum to characterize the sample.

18. A method according to claim 17, wherein:
said first transform is a Fourier transform and said second transform is a Laplace inversion, and said processing comprises Fourier transforming said obtained signal over τ1 and Laplace inverting said Fourier transformed signal over τ2 in order to obtain said multi-dimensional spectrum, where τ2 is equal to N*te.

19. A method according to claim 18, wherein:
said using comprises displaying said multi-dimensional spectrum as a graph with chemical shift as one axis and T2 relaxation time as another axis.

20. A method according to claim 18, wherein:
said using comprises obtaining weight percentages of a plurality of molecular species from said multi-dimensional spectrum and displaying an indication of said weight percentages.

21. A method according to claim 17, wherein the sample is a hydrocarbon sample.

22. A method according to claim 21, wherein:
said using comprises determining relaxation rates of aromatic protons, and from said relaxation rates, determining the presence of asphaltenes in said hydrocarbon sample.

23. A method according to claim 22, wherein:
said using further comprises determining a concentration of asphaltenes in said hydrocarbon sample based on said relaxation rates of said aromatic protons.

24. A method for characterizing a sample containing a plurality of molecular species, the method comprising:
subjecting the sample to a nuclear magnetic resonance (NMR) field according to an NMR pulse sequence that includes (i) an NMR spectroscopy portion and (ii) an NMR spin-lattice relaxation time T1 portion, where said pulse sequence is π-τ2-π/2-τ1(ACQ), where m is a hundred-eighty degree pulse, τ2 is a time period that is incremented multiple times during an experiment, π/2 is a ninety degree pulse, τ1 is a spectroscopy time period that is incremented multiple times during the experiment, and τ1(ACQ) refers to acquisition of a spectroscopy signal during the spectroscopy time period;

measuring a measured signal resulting from an interaction of said NMR field according to said NMR pulse sequence and the sample;

processing the measured signal using a first transform over a spectroscopy variable and using a second transform over an NMR relaxation variable to obtain a multi-dimensional spectrum; and using the multi-dimensional spectrum to characterize the sample.

25. A method according to claim 24, wherein:
said first transform is a Fourier transform and said second transform is a Laplace inversion, and said processing comprises Fourier transforming said obtained signal over τ1 and Laplace inverting said Fourier transformed signal over τ2 in order to obtain said multi-dimensional spectrum.

26. A method according to claim 25, wherein:
said using comprises obtaining weight percentages of a plurality of molecular species from said multi-dimensional spectrum and displaying an indication of said weight percentages.

27. A method according to claim 24, wherein:
said using comprises displaying said multi-dimensional spectrum as a graph with chemical shift as one axis and said T1 relaxation time as another axis.

28. A method according to claim 24, wherein the sample is a hydrocarbon sample.

29. A method according to claim 28, wherein:
said using comprises determining relaxation rates of aromatic protons, and from said relaxation rates, determining the presence of asphaltenes in said hydrocarbon sample.

30. A method according to claim 29, wherein:
said using further comprises determining a concentration of asphaltenes in said hydrocarbon sample based on said relaxation rates of said aromatic protons.

31. A method for characterizing a sample containing a plurality of molecular species, the method comprising:
subjecting the sample to a nuclear magnetic resonance (NMR) field according to an NMR pulse sequence that includes (i) an NMR spectroscopy portion and (ii) an NMR spin-lattice relaxation time T1 portion, wherein said pulse sequence further includes an NMR diffusion portion and said pulse sequence is $\pi/2\text{-}te_1/2\text{-}\pi\text{-}te_1/2\text{-}te/2\text{-}\{\pi\text{-}te\}_N\text{-}te/2\text{-}\tau1(ACQ)$, where π/2 is a ninety degree pulse, $te_1$ is a first echo time, π is a hundred-eighty degree pulse, te is a second echo time, N is a number of repetitions that is incremented multiple times during an experiment, τ1 is a spectroscopy time period that is incremented multiple times during the experiment, and τ1(ACQ) refers to acquisition of a spectroscopy signal during the spectroscopy time period, and wherein a first field gradient pulse is applied during a first time period $te_1/2$, a second field gradient pulse is applied during a second time period $te_1/2$, the first field gradient pulse and second field gradient pulse have equal durations (d) and amplitudes (g), and the amplitudes (g) are incremented multiple times during the experiment;

measuring a measured signal resulting from an interaction of said NMR field according to said NMR pulse sequence and the sample;

processing the measured signal using a first transform over a spectroscopy variable and using a second transform over an NMR relaxation variable to obtain a multi-dimensional spectrum; and using the multi-dimensional spectrum to characterize the sample.

32. A method according to claim 31, wherein:
said first transform is a Fourier transform and said second transform is a 2D Laplace inversion, and said processing comprises Fourier transforming said obtained signal along a τ1 direction and then 2D Laplace inverting said Fourier transformed signal along the τ2 and b directions simultaneously thereby generating said multi-dimensional spectrum, wherein b is an NMR diffusion-related term and τ2 is equal to N*te.

33. A method according to claim 32, wherein:

$$b = \gamma^2 g^2 d^2 \left(\Delta - \frac{d}{3}\right),$$

where γ is the gyromagnetic ratio of nuclei of the sample and Δ is the time delay between a rising edge of the first field gradient pulse and a rising edge of the second field gradient pulse.

34. A method according to claim 32, wherein:
said using comprises displaying said multi-dimensional spectrum as a graph with chemical shift as one axis, T2 relaxation time as another axis, and diffusion D as another axis.

35. A method according to claim 31, wherein:
said using comprises obtaining weight percentages of a plurality of molecular species from said multi-dimensional spectrum and displaying an indication of said weight percentages.

36. A method according to claim 31, wherein the sample is a hydrocarbon sample.

37. A method according to claim 36, wherein:
said using comprises determining relaxation rates of aromatic protons, and from said relaxation rates, determining the presence of asphaltenes in said hydrocarbon sample.

38. A method according to claim 37, wherein:
said using further comprises determining a concentration of asphaltenes in said hydrocarbon sample based on said relaxation rates of said aromatic protons.

39. A method for characterizing a sample containing a plurality of molecular species, the method comprising:
subjecting the sample to a nuclear magnetic resonance (NMR) field according to an NMR pulse sequence that includes (i) an NMR spectroscopy portion and (ii) an NMR relaxation portion;
measuring a measured signal resulting from an interaction of said NMR field according to said NMR pulse sequence and the sample;
parameterizing a distribution function in terms of a plurality of parameters for said plurality of molecular species;
using a forward model related to said pulse sequence to calculate an expected signal for an estimated combination of said plurality of molecular species;
comparing with a processor the expected signal to said measured signal to obtain a difference; and
iteratively adjusting said plurality of parameters and repeating said using a forward model and said comparing to reduce said difference, to obtain a characterization of said sample.

40. A method according to claim 39, wherein:
said adjusting is repeated until said expected signal generated from said model is consistent with said measured signal.

41. A method according to claim 40, wherein:
said adjusting is repeated until a best fit is found for said plurality of parameters.

42. A method according to claim 41, further comprising:
displaying an indication of the quantities of molecular species contained in the sample.

* * * * *